US007320786B2

(12) United States Patent
Chen (10) Patent No.: US 7,320,786 B2
(45) Date of Patent: Jan. 22, 2008

(54) PHOTODYNAMIC THERAPY TREATMENT FOR EYE DISEASE

(75) Inventor: James C. Chen, Bellevue, WA (US)

(73) Assignee: Light Sciences Oncology, Inc., Snoqualmie, WA (US)

( * ) Notice: Subject to any disclaimer, the term of this patent is extended or adjusted under 35 U.S.C. 154(b) by 0 days.

(21) Appl. No.: 11/297,880

(22) Filed: Dec. 7, 2005

(65) Prior Publication Data

US 2006/0088530 A1    Apr. 27, 2006

Related U.S. Application Data

(63) Continuation-in-part of application No. 09/760,362, filed on Jan. 12, 2001, now abandoned.

(60) Provisional application No. 60/175,689, filed on Jan. 12, 2000.

(51) Int. Cl.
*A61K 9/00* (2006.01)
*A61K 39/395* (2006.01)
*A01N 43/38* (2006.01)

(52) U.S. Cl. .................. 424/9.6; 424/9.61; 424/143.1; 424/178.1; 514/185; 514/912

(58) Field of Classification Search ...................... None
See application file for complete search history.

(56) References Cited

U.S. PATENT DOCUMENTS

| | | | |
|---|---|---|---|
| 3,817,837 A | 6/1974 | Rubinstein et al. |
| 4,374,925 A | 2/1983 | Litman et al. |
| 4,521,762 A | 6/1985 | Kapral |
| 4,577,636 A | 3/1986 | Spears |
| 4,753,958 A | 6/1988 | Weinstein et al. |
| 4,823,244 A | 4/1989 | Alaybayoglu et al. |
| 4,861,876 A | 8/1989 | Kessel |
| 4,878,891 A | 11/1989 | Judy et al. |
| 4,932,934 A | 6/1990 | Dougherty et al. |
| 4,957,481 A | 9/1990 | Gatenby |
| 4,961,920 A | 10/1990 | Ward |
| 4,997,639 A | 3/1991 | Aizawa et al. |
| 5,002,962 A | 3/1991 | Pandey et al. |
| 5,026,367 A | 6/1991 | Leckrone et al. |
| 5,028,594 A | 7/1991 | Carson |
| 5,041,078 A | 8/1991 | Matthews et al. |
| 5,053,006 A | 10/1991 | Watson |
| 5,171,749 A | 12/1992 | Levy et al. |
| 5,222,795 A | 6/1993 | Hed |
| 5,238,940 A | 8/1993 | Liu et al. |
| 5,263,925 A | 11/1993 | Gilmore, Jr. et al. |
| 5,283,255 A | 2/1994 | Levy et al. |
| 5,298,018 A | 3/1994 | Narciso, Jr. |
| 5,308,861 A | 5/1994 | Aizawa et al. |
| 5,314,905 A | 5/1994 | Pandey et al. |
| 5,330,741 A | 7/1994 | Smith et al. |
| 5,368,841 A | 11/1994 | Trauner et al. |
| 5,399,583 A | 3/1995 | Levy et al. |
| 5,430,051 A | 7/1995 | Aizawa et al. |
| 5,441,531 A | 8/1995 | Zarate et al. |
| 5,445,608 A | 8/1995 | Chen et al. |
| 5,456,661 A | 10/1995 | Narciso, Jr. |
| 5,459,159 A | 10/1995 | Pandey et al. |
| 5,474,765 A | 12/1995 | Thorpe |
| 5,482,698 A | 1/1996 | Griffiths |
| 5,484,778 A | 1/1996 | Kenney et al. |
| 5,484,803 A | 1/1996 | Richter |
| 5,494,793 A | 2/1996 | Schindele et al. |
| 5,498,710 A | 3/1996 | Pandey et al. |
| 5,500,009 A | 3/1996 | Mendes et al. |
| 5,503,637 A | 4/1996 | Kyricos et al. |
| 5,514,669 A | 5/1996 | Selman |
| 5,534,506 A | 7/1996 | Morgan et al. |
| 5,543,514 A | 8/1996 | Sessler et al. |
| 5,549,660 A | 8/1996 | Mendes et al. |
| 5,556,612 A | 9/1996 | Anderson et al. |
| 5,565,552 A | 10/1996 | Magda et al. |
| 5,567,409 A | 10/1996 | Aizawa et al. |
| 5,571,152 A | 11/1996 | Chen et al. |
| 5,576,013 A | 11/1996 | Williams et al. |
| 5,591,847 A | 1/1997 | Pandey et al. |
| 5,594,136 A | 1/1997 | Sessler et al. |
| 5,616,140 A | 4/1997 | Prescott |
| 5,616,719 A | 4/1997 | Davalian et al. |
| 5,618,732 A | 4/1997 | Pease et al. |
| 5,624,909 A | 4/1997 | Rao et al. |
| 5,630,996 A | 5/1997 | Reno et al. |
| 5,633,275 A | 5/1997 | Mori et al. |
| 5,634,711 A | 6/1997 | Kennedy et al. |

(Continued)

FOREIGN PATENT DOCUMENTS

AU    0674251    12/1996

(Continued)

OTHER PUBLICATIONS

Blaauwgeers et al, Am J Pathology 155(2): 421-428, 1999.*

(Continued)

*Primary Examiner*—Christina Chan
*Assistant Examiner*—Phuong Huynh
(74) *Attorney, Agent, or Firm*—McAndrews, Held & Malloy, Ltd.

(57) ABSTRACT

This invention discloses methods, kits, and instructions to treat neovasculature diseases of the eye through the administration of a targeted photosensitizing agent and subsequent exposure to light of specific wavelength sufficient to photoactivate photosensitizing agent. The photosensitizing agent is bound to a composition that mediates site specific delivery to a neovasculature target tissue of a therapeutically effective amount of a photosensitizing agent that is activated by a relatively low fluence rate of light over a prolonged period of time. Diseases treatable under this invention, include: diabetic retinopathy; macular degeneration; and malignant uveal melanomas.

17 Claims, 3 Drawing Sheets

U.S. PATENT DOCUMENTS

| | | | |
|---|---|---|---|
| 5,702,432 A | 12/1997 | Chen et al. | |
| 5,705,518 A | 1/1998 | Richter et al. | |
| 5,707,401 A | 1/1998 | Talmore | |
| 5,715,837 A | 2/1998 | Chen | |
| 5,735,817 A | 4/1998 | Shantha | |
| 5,736,563 A | 4/1998 | Richter | |
| 5,741,316 A | 4/1998 | Chen et al. | |
| 5,746,494 A | 5/1998 | Koeda et al. | |
| 5,746,495 A | 5/1998 | Klamm | |
| 5,756,541 A * | 5/1998 | Strong et al. | 514/502 |
| 5,766,234 A | 6/1998 | Chen et al. | |
| 5,770,619 A | 6/1998 | Richter et al. | |
| 5,776,175 A | 7/1998 | Eckhouse et al. | |
| 5,782,896 A | 7/1998 | Chen et al. | |
| 5,797,868 A | 8/1998 | Leone | |
| 5,798,349 A | 8/1998 | Levy et al. | |
| 5,800,478 A | 9/1998 | Chen et al. | |
| 5,803,575 A | 9/1998 | Ansems et al. | |
| 5,807,881 A | 9/1998 | Leong et al. | |
| 5,814,008 A | 9/1998 | Chen et al. | |
| 5,817,048 A | 10/1998 | Lawandy | |
| 5,824,080 A | 10/1998 | Lamuraglia | |
| 5,827,186 A | 10/1998 | Chen et al. | |
| 5,827,819 A | 10/1998 | Yatvin et al. | |
| 5,829,448 A | 11/1998 | Fisher et al. | |
| 5,832,931 A | 11/1998 | Wachter et al. | |
| 5,835,648 A | 11/1998 | Narciso, Jr. et al. | |
| 5,840,301 A * | 11/1998 | Rockwell et al. | 424/143.1 |
| 5,843,143 A | 12/1998 | Whitehurst | |
| 5,851,225 A | 12/1998 | Lawandy | |
| 5,855,866 A | 1/1999 | Thorpe et al. | |
| 5,864,035 A | 1/1999 | Pandey et al. | |
| 5,865,840 A | 2/1999 | Chen | |
| 5,869,457 A | 2/1999 | Jansen et al. | |
| 5,876,427 A | 3/1999 | Chen et al. | |
| 5,877,279 A | 3/1999 | Goldberg | |
| 5,882,328 A | 3/1999 | Levy et al. | |
| 5,906,579 A | 5/1999 | Vander Salm et al. | |
| 5,910,510 A * | 6/1999 | Strong et al. | 514/502 |
| 5,912,257 A | 6/1999 | Prasad et al. | |
| 5,913,834 A | 6/1999 | Francais | |
| 5,913,884 A | 6/1999 | Trauner et al. | |
| 5,919,217 A | 7/1999 | Hughes | |
| 5,921,244 A | 7/1999 | Chen et al. | |
| 5,929,105 A | 7/1999 | Dolphin et al. | |
| 5,942,534 A | 8/1999 | Trauner et al. | |
| 5,944,748 A | 8/1999 | Mager et al. | |
| 5,945,439 A | 8/1999 | Richter et al. | |
| 5,945,762 A | 8/1999 | Chen et al. | |
| 5,952,366 A | 9/1999 | Pandey et al. | |
| 5,955,585 A | 9/1999 | Scherz et al. | |
| 5,957,960 A | 9/1999 | Chen et al. | |
| 5,961,543 A | 10/1999 | Waldmann | |
| 5,976,175 A | 11/1999 | Hirano et al. | |
| 5,976,535 A * | 11/1999 | Fritzberg et al. | 424/182.1 |
| 5,989,245 A | 11/1999 | Prescott | |
| 5,994,535 A | 11/1999 | Sessler et al. | |
| 5,997,569 A | 12/1999 | Chen et al. | |
| 5,997,842 A | 12/1999 | Chen | |
| 5,998,597 A | 12/1999 | Fisher et al. | |
| 6,015,897 A | 1/2000 | Theodore et al. | |
| 6,021,347 A | 2/2000 | Herbst et al. | |
| 6,036,941 A | 3/2000 | Bottiroli et al. | |
| 6,048,359 A | 4/2000 | Biel | |
| 6,051,230 A | 4/2000 | Thorpe et al. | |
| 6,058,937 A | 5/2000 | Doiron et al. | |
| 6,071,944 A | 6/2000 | Rodgers et al. | |
| 6,080,160 A | 6/2000 | Chen et al. | |
| 6,083,485 A | 7/2000 | Licha et al. | |
| 6,090,788 A | 7/2000 | Lurie | |
| 6,092,531 A | 7/2000 | Chen et al. | |
| 6,096,066 A | 8/2000 | Chen et al. | |
| 6,100,290 A | 8/2000 | Levy et al. | |
| 6,107,325 A | 8/2000 | Chan et al. | |
| 6,107,466 A | 8/2000 | Hasan et al. | |
| 6,117,862 A | 9/2000 | Margaron et al. | |
| 6,123,923 A | 9/2000 | Unger et al. | |
| 6,135,620 A | 10/2000 | Marsh | |
| 6,138,681 A | 10/2000 | Chen et al. | |
| 6,152,951 A | 11/2000 | Hashimoto et al. | |
| 6,162,242 A | 12/2000 | Peyman | |
| 6,187,030 B1 | 2/2001 | Gart et al. | |
| 6,210,425 B1 | 4/2001 | Chen | |
| 6,217,869 B1 | 4/2001 | Meyer et al. | |
| RE37,180 E | 5/2001 | Mori et al. | |
| 6,238,426 B1 | 5/2001 | Chen | |
| 6,270,749 B1 * | 8/2001 | Blumenkranz et al. | 424/9.61 |
| 6,273,904 B1 | 8/2001 | Chen et al. | |
| 6,281,611 B1 | 8/2001 | Chen et al. | |
| 6,297,228 B1 | 10/2001 | Clark | |
| 6,319,273 B1 | 11/2001 | Chen et al. | |
| 6,331,744 B1 | 12/2001 | Chen et al. | |
| 6,344,050 B1 | 2/2002 | Chen | |
| 6,416,531 B2 | 7/2002 | Chen | |
| 6,454,789 B1 | 9/2002 | Chen et al. | |
| 6,520,669 B1 | 2/2003 | Chen et al. | |
| 6,554,853 B2 | 4/2003 | Chen | |
| 6,580,228 B1 | 6/2003 | Chen et al. | |
| 6,602,274 B1 | 8/2003 | Chen | |
| 6,624,187 B1 | 9/2003 | Pandey et al. | |
| 6,657,351 B2 | 12/2003 | Chen et al. | |
| 6,899,723 B2 * | 5/2005 | Chen | 607/88 |
| 7,018,395 B2 | 3/2006 | Chen | |
| 2001/0044623 A1 | 11/2001 | Chen | |
| 2001/0046983 A1 | 11/2001 | Pandey et al. | |
| 2001/0049502 A1 | 12/2001 | Chen | |
| 2002/0010500 A1 | 1/2002 | Chen | |
| 2002/0049247 A1 | 4/2002 | Chen | |
| 2002/0087205 A1 | 7/2002 | Chen | |
| 2002/0088980 A1 | 7/2002 | Wipiejewski | |
| 2002/0127224 A1 | 9/2002 | Chen | |
| 2002/0127230 A1 | 9/2002 | Chen | |
| 2002/0128303 A1 | 9/2002 | Bellnier | |
| 2002/0193576 A1 | 12/2002 | Chen | |
| 2002/0198576 A1 | 12/2002 | Chen | |
| 2003/0018371 A1 | 1/2003 | Chen | |
| 2003/0030342 A1 | 2/2003 | Chen et al. | |
| 2003/0109813 A1 | 6/2003 | Chen | |
| 2003/0114434 A1 | 6/2003 | Chen et al. | |
| 2003/0167033 A1 | 9/2003 | Chen et al. | |
| 2003/0208249 A1 | 11/2003 | Chen | |
| 2004/0044197 A1 | 3/2004 | Pandey et al. | |
| 2004/0044198 A1 | 3/2004 | Pandey et al. | |
| 2005/0004510 A1 | 1/2005 | Chen | |

FOREIGN PATENT DOCUMENTS

| | | |
|---|---|---|
| AU | 0694868 | 7/1998 |
| AU | 0708410 | 8/1999 |
| AU | 0713227 | 11/1999 |
| AU | 0720815 | 6/2000 |
| AU | 0721857 | 7/2000 |
| EP | 0175617 A2 | 3/1986 |
| EP | 0175617 B1 | 3/1986 |
| EP | 0407122 A1 | 1/1991 |
| EP | 0407122 B1 | 1/1991 |
| EP | 03010382.4 | 5/2003 |
| JP | 51-159879 | 7/1978 |
| JP | 57-185220 | 11/1982 |
| WO | 92/00106 | 1/1992 |
| WO | WO 92/00106 | 1/1992 |
| WO | 9311657 | 6/1993 |
| WO | 9406424 | 3/1994 |
| WO | 9409851 | 5/1994 |

| | | |
|---|---|---|
| WO | 9505214 | 2/1995 |
| WO | 9532001 | 11/1995 |
| WO | 9606641 | 3/1996 |
| WO | 9637255 | 11/1996 |
| WO | 97/31582 | 9/1997 |
| WO | 9732520 | 9/1997 |
| WO | WO 97/31582 | 9/1997 |
| WO | 9740679 | 11/1997 |
| WO | 9746262 | 12/1997 |
| WO | 9804317 | 2/1998 |
| WO | 9806456 | 2/1998 |
| WO | 9808565 | 3/1998 |
| WO | 9814243 | 4/1998 |
| WO | 9824371 | 6/1998 |
| WO | 9824510 | 6/1998 |
| WO | 9832491 | 7/1998 |
| WO | 9832492 | 7/1998 |
| WO | 9832493 | 7/1998 |
| WO | 9846130 | 10/1998 |
| WO | 9847541 | 10/1998 |
| WO | 9850034 | 11/1998 |
| WO | 9850387 | 11/1998 |
| WO | 9852610 | 11/1998 |
| WO | 9856302 | 12/1998 |
| WO | 9903503 | 1/1999 |
| WO | 9918879 | 4/1999 |
| WO | 9920346 | 4/1999 |
| WO | 9939769 | 8/1999 |
| WO | 9952565 | 10/1999 |
| WO | 9958149 | 11/1999 |
| WO | 99/67249 A1 | 12/1999 |
| WO | 9966988 | 12/1999 |
| WO | 0012538 | 3/2000 |
| WO | 0015296 | 3/2000 |
| WO | 0036983 | 6/2000 |
| WO | 0041725 | 7/2000 |
| WO | 0041726 | 7/2000 |
| WO | 0041727 | 7/2000 |
| WO | 0041768 | 7/2000 |
| WO | 0052793 | 9/2000 |
| WO | 00/61584 A1 | 10/2000 |
| WO | 0103770 | 1/2001 |
| WO | 0105316 | 1/2001 |
| WO | 0115694 | 3/2001 |
| WO | 0143825 | 6/2001 |
| WO | 0151087 | 7/2001 |
| WO | 0178216 | 10/2001 |
| WO | 0178458 | 10/2001 |
| WO | 0198708 | 12/2001 |
| WO | 0217690 | 2/2002 |
| WO | PCT US02/28149 | 11/2002 |
| WO | PCT/US03 02303 | 1/2003 |
| WO | 03/052793 A2 | 6/2003 |
| WO | 03052793 | 6/2003 |
| WO | WO 03/052793 | 6/2003 |
| WO | PCT/US03/21179 | 7/2003 |
| WO | WO 03/061696 | 7/2003 |
| WO | 2004/002476 A2 | 1/2004 |
| WO | 2004/005289 A2 | 1/2004 |
| WO | WO 2004/002486 | 1/2004 |
| WO | WO 2004005289 | 1/2004 |

OTHER PUBLICATIONS

Boulton et al., "VEGF localisation in diabetic retinopathy," *Br. J. Opthalmol.* 82:561-568 (1998).
Certified English Translation of: Fischer, H. et al., "[On the Bromination of the Esters of Mesoisochlorin $e_4$ and Mesochlorin $e_6$]," *Berischte der Deutschen Chemischen* 75:1778-1795 (1942).
Chen et al., "New directions in photodynamic therapy," *ICCP-2. 2nd International Conference on Porphyrins and Phthalocyanines*, Jun. 30-Jul. 5, 2002; Kyoto, Japan: 78 [abstract S-26].
Chen et al., "New technology for deep light distribution in tissue for phototherapy," *Cancer J* 8(2):154-163. (2002).
Chen et al., "Next-generation light delivery system for multitreatment extended-duration photodynamic therapy (MED-PDT)," *Proc SPIE* 2972:161-166 (1997).
Database Crossfire Beilstein, Database Acession No. 4286587 (Reaction ID), for Levinson, E.G. et al., Russ. J. Bioorg. Chem (Engl. Transl.) 21(3):199-203 (1995) in Russian in the :Bioorg. Khim. 21(3):230-234 (1995).
Derwent English Abstract, Accession No. 1996-475153, citing Russian Patent RU 2054944 C, published Feb. 27, 1996, "Production of purpurin-18 for treatment of tumours—comprises extracting vegetable waste with ethanol, oxidative splitting, degreasing and purifying".
Devoisselle, J.M et al., "Effect of indocyanin green formulation on blood clearance and in vivo fluorescence kinetic profile of skin," Proceedings of optical biopsies : Sep. 14-15, 1995, Barcelona, Spain SPIE proceedings series, v. 2627 pp. 100-108 (1995).
Dougherty et al., "Photosensitization of Malignant Tumors," *Seminars in Surgical Oncology* 2:24-37 (1984).
Fischer, H. et al., "[On the Bromination of the Esters of Mesoisochlorin $e_4$ and Mesochlorin $e_6$]," *Berischte der Deutschen Chemischen* 75:1778-1795 (1942).
Haslam et al., "Recent Developments in Methods for the Esterification and Protection of the Carboxyl Group," *Tetrahedron* 36: 2409-2433 (1980).
Henderson et al., "An in Vivo Quantitative Structure-Activity Relationship for a Congeneric Series of Pyropheophorbide Derivatives as Photosensitizers for Photodynamic Therapy," *Cancer Research* 57:4000-4007 (1997).
Kessel et al., "Photosensitization with Bacteriochlorins," *Photochemistry and Photobiology* 58(2):200-203 (1993).
Kreimer-Birnbaum et al., "Modified Porphyrins, Chlorins, Phthalocyanines, and Purpurins: Second-Generation Photosensitizers for Photodynamic Therapy," *Seminars in Hematology* 26(2):157-173 (1989).
Li et al., "Application of Ruppert's reagent in preparing novel perfluorinated porphyrins, chlorins and bacteriochlorins", *J. Chem. Soc. Perkin Trans* 1, 1785-1787 (1999).
Pandey et al., "Comparative in vivo Sensitizing Efficacy of Porphyrin and Chlorin Dimers Joined with Ester, Ether, Carbon-Carbon or Amide Bonds," Journal of Molecular Recognition 9:118-122 (1996).
Patent Abstract of Japan citing Japanese Patent Application JP 09124652, published May 13, 1997, "Porphyrin Derivative and Use Thereof".
Prewett et al., "Antivascular Endothelial Growth Factor Receptor (Fetal Liver Kinase 1) Monoclonal Antibody Inhibits Tumor Angiogenesis and Growth of Several Mouse and Human Tumors" Cancer Research 59:5209-5218 (1999).
Rakestraw et al., "Antibody-targeted photolysis: In vitro studies with Sn(IV) chlorin e6 covalently bound to monoclonal antibodies using a modified dextran carrier," Proc. Natl. Acad. Sci. USA 87:4217-4221 (1990).
Schmidt-Erfurth et al., "Photodynamic therapy of subfoveal choroidal neovascularization: clinical and angiographic examples," *Graefe's Arch Clin Exp Opthalmol.* 236:365-374 (1998).
Schmidt-Erfurth et al., "Vascular Targeting in Photodyamic Occlusion of Subretinal Vessels," *Opthalmology* 101:1953-1961 (1994).
Smith et al., "Bacteriochlorophylls *c* from *Chloropseudomonas ethylicum*. Composition and NMR Studies of the Pheophorbides and Derivatives," *Journal of the American Chemical Society* 102(7):2437-2448 (1980).
Smith et al., "*Meso* substitution of chlorophyll derivatives : direct route for transformation of bacteriopheophorbides *d* into bacteriopheophorbides *c,*" *Journal of the American Chemical Society* 107:4946-4954 (1985).
Spikes, J.D., "Porphyrins and Related Compounds as Photodynamic Sensitizers," Annals of the New York Academy of Sciences 244:496-508 (1975).

Zheng et al., "Photosensitizers Related to Purpurin-18-*N*-alkylimides: A Comparative in vivo Tumoricidal Ability of Ester versus Amide Functionalities", *Bioorganic & Med. Chem. Letts.*, 10:123-127 (2000).

Zheng et al., "Chlorin-based symmetrical and unsymmetrical dimers with amide linkages: effect of the substituents on photodynamic and photophysical properties," *J. Chem. Soc. Perkins. Trans.* 1, 3113-3121 (2000).

U.S. Appl. No. 09/739,155, filed Dec. 18, 2000.
U.S. Appl. No. 09/592,150, filed Jun. 12, 2000.
U.S. Appl. No. 09/801,163, filed Mar. 7, 2001.
U.S. Appl. No. 10/351,730, filed Jan. 23, 2003.
U.S. Appl. No. 10/211,784, filed Aug. 1, 2002.
U.S. Appl. No. 09/271,575, filed Mar. 18, 1999.
U.S. Appl. No. 09/905,501, filed Jul. 13, 2001.
U.S. Appl. No. 10/317,269, filed Dec. 10, 2002.
U.S. Appl. No. 09/905,777, filed Jul. 13, 2001.
U.S. Appl. No. 09/905,405, filed Jul. 13, 2001.
U.S. Appl. No. 09/386,692, filed Aug. 31, 1999.
U.S. Appl. No. 09/798,277, filed Feb. 6, 2002.
U.S. Appl. No. 10/091,144, filed Mar. 4, 2002.
U.S. Appl. No. 09/078,329, filed May 13, 1998.
U.S. Appl. No. 09/150,821, filed Sep. 11, 1998.
U.S. Appl. No. 09/597,931, filed Jun. 19, 2000.
U.S. Appl. No. 09/644,253, filed Aug. 22, 2000.
U.S. Appl. No. 09/910,364, filed Jul. 20, 2001.
U.S. Appl. No. 10/021,891, filed Dec. 12, 2001.
U.S. Appl. No. 10/384,895, filed Mar. 7, 2003.
U.S. Appl. No. 10/385,378, filed Mar. 7, 2003.
U.S. Appl. No. 10/410,700, filed Apr. 8, 2003.

De Jode, et al., "A comparison of Novel Light Sources for Photodynamic Therapy", Lasers Med Sci, 12:260-268 (1997).

Mizeret, et al., "Cylindrical Fiberoptic Light Diffuser for Medical Application", Lasers Surg. Med., 19:159-167 (1996).

Kramer et al, Ophthalmology 103(3): 427-38, Mar. 1996.

Adili et al., "Local delivery of photosensitizing drugs in arteries: a novel approach to photodynamic therapy for the prevention of intimal hyperplasia", *Proc. SPIE-INT. Scc. Opt. Eng.*, 2395:402-408 (1995).

Birchler et al., "Selective Targeting and Photocoagulation of Ocular Angiogenesis Mediated by a Phage-Derived Human Antibody Fragment", *Nature Biotechnol.*, 17:984-988 (1999).

Chen, J., Next Generation Light Delivery System for Multi-Treatment Extended Duration Photodynamic Therapy (MED-PDT), *SPIE-Proceedings Series*, 2972:161-167 (1997).

Ciulla et al., "Changing therapeutic paradigms for exudative age-relted macular degeneration: antiangiogenic agents and photodynamic therapy", *Exp. Opin. Invest. Drugs*, 8(12):2173-2182 (1999).

Dartsch et al., "Photodynamic therapy of vascular stenoses: Response of cultured human smooth muscle cells from non-atherosclerotic arteries and atheromatous plaques following treatment with photosensitizing porphyrins", *Proc. SPIE-INT. Scc. Opt. Eng.*, 1462:77-80 (1990).

Dimitroff et al., "Anti-angiogenic activity of selected receptor tyrosine kinase inhibitors, PD166285 and PD173074: Implications for combination treatment with photodynamic therapy", *Investigational New Drugs*, 17:121-135 (1999).

Dougherty et al., Yearly Review "Photodynamic Therapy", *Photochem. Photobiol.*, 58(6):895-900 (1993).

Dougherty et al., Review "Photodynamic Therapy", *J. Natl. Cancer Inst.*, 90(12):889-905 (1998).

Ferrario et al., "Antiangiogenic Treatment Enhances Photodynamic Therapy Responsiveness in a Mouse Mammary Carcinoma", *Cancer Research*, 60:4066-4069 (2000).

Granville et al., "Photodynamic treatment with benzoporphyrin derivative monoacid ring A produces protein tyrosine phosphorylation events and DNA fragmentation in murine P815 cells", *Photochem. Photobiol.*, 67(3):358-362 (1998).

Jiang et al., "Enhanced Photodynamic Killing of Target Cells by Either Monoclonal Antibody or Low Density Lipoprotein Mediated Delivery Systems", *J. Controlled Release*, 19(1/3):41-58 (1992).

Jiang et al., "Selective depletion of a thymocyte subset in vitro with an immunomodulatory photosensitizer", *Clinical Immunol.*, 91(2):178-187 (1999).

Marcus, S.L., "Photodynamic Therapy of Human Cancer", *Proc. IEEE*, 80(6):869-889 (1992).

Margaron et al., "Photodynamic therapy inhibits cell adhesion without altering integrin expression", *Biochem. Biophys. ACTA*, 1359(3):200-210 (1997).

McMillan et al., "Tumor growth inhition and regression induced by photothermal vascular targeting and angiogenesis inhibitor retinoic acid", *Cancer Lett.*, 137:35-44 (1999).

Meerovich et al., "Photosensitizer for PDT based on phosphonate phthalocyanine derivative", *Proc. SPIE-INT. Scc. Opt. Eng.*, 2924:86-90 (1996).

Mew et al., "Photoimmunotherapy: Treatment of Animal Tumors with Tumor-Specific Monoclonal Antibody-Hematoporphyrin Conjugates", *J. Immunol.*, 130(3):1473-1477 (1983).

Millson, C.E. et al. "Ex-Vivo Treatment of Gastric Helicobacter Infection by Photodynamic Therapy," *J. Photochem. Photobiol. B: Biol.*, 32:59-65 (1996).

Nemoto et al., "Inhibition by a new bisphosphonate (YM175) of bone resorption induced by the MBT-2 tumor of mice", *Brit. J. Cancer*, 67(5):893-897 (1993).

Pandey et al., "Shedding some light on tumors", *Chem. Indust.*, 1998:739-743, (1998).

Renno et al., "Photodynamic Therapy Using Lu-Tex Induces Apoptosis In Vitro, and Its Effect is Potentiated by Angiostatin in Retinal Capillary Endothelial Cells", *Investigative Opthalmol. & Visual Sci.*, 41(12):3963-3971 (2000).

Savellano et al., "Pegylated BPD verteporfin C225 anti-EGF receptor direct covalent linkage photosensitizer immunoconjugates", *Photochem. Photobiol.*, 69(Spec. Issue):38S (1999).

Schmidt-Erfurth et al., "InVivo Uptake of Liposomal Benzoporphyrin Derivative and Photothrombosis in Experimental Corneal Neovascularization", *Lasers in Surgery and Medicine*, 17:178-188 (1995).

Schmidt-Erfurth et al., "Photodynamic therapy of experimental choroidal melanoma using lipoprotein-delivered benzoporphyrin", *Ophthalmol.*, 101(1):89-99 (1994).

Sharman et al., "Novel water-soluble phthalocyanines substituted with phosphonate moieties on the benzo rings", *Tetrahedron Lett.*, 37(33):5831-5834 (1996).

Sternberg et al., "Porphyrin-based Photosensitizers for Use in Photodynamic Therapy", *Tetrahedron*, 54(17):4151-4202 (1998).

Barr et al., "Normal Tissue Damage Following Photodynamic Therapy: Are There Biological Advantages?", Photodynamic Therapy, Basic Principles and Clinical Applications, Henderson, Barbara W. and Dougherty, Thomas J., (Eds.); Marcel Dekker, Inc., New York; pp. 201-216.

Gilson et al., "Therapeutic ratio of photodynamic therapy in the treatment of superficial tumours of skin and subcutaneous tissues in man", *J. Cancer*, 58:665-667 (1988).

Haas et al., "Phototherapy of Bladder Cancer: Dose/Effect Relationships", Journal of Urology, 136:525-528 (1986).

Lin et al., "Skin Necrosis due to Photodynamic Action of Benzoporphyrin Depends on Circulating Rather than Tissue Drug Levels: Implications for Control of Photodynamic Therapy", *Photochem. Photobiol.*, 68(4):575-583 (1998).

Mew et al., "Ability of Specific Monoclonal Antibodies and Conventional Antisera Conjugated to Hematoporphyrin to Label and Kill Selected Cell Lines Subsequent to Light Activation", *Cancer Res.*, 45:4380-4386 (1985).

Parrish, J.A. "Photobiologic Consideration in Photoradiation Therapy," *Porphyrin Photosensitization*, Plenum Press, 91-108 (1983).

Tomio et al., "Effect of Hematoporphyrin and Red Light on AH-130 Solid Tumors in Rats", *ACTA Radiologica Oncol.*, 22:49-53 (1983).

Yumita et al., "The Combination Treatment of Ultrasound and Antitumor Drugs on Yoshida Sarcoma", *Japan J. Hyperthermic Oncol.*, 3(2):175-182 (1987).

Nakatani, Y. et al., (1981) "Chemistry and biochemistry of Chinese drugs. VII. Cytostatic pheophytins from silkworm excreta, and derived photocytotoxic pheophorbides" *Chem. Pharm. Bull.* 29(8):2261-2269.

Yamamoto, T. (Dec. 10, 1974) "Effect of phytochlorin on transplantable cancer cells" *Medicine and Biology* 89(6):433-438, English translation and certificate of translation included, 7 pages.

Yamamoto, T. (Apr. 10, 1975) "Suppression of tumors by the photodynamic action of phytochlorin sodium" *Medicine and Biology* 90(4):161-164, English translation and certificate of translation included, 4 pages.

Yamamoto, T. and Miyagawa, F. (Jun. 10, 1975) "Photodynamic effects on the nucleic acids of cancer cells sensitized by sodium phytochlorin" *Medicine and Biology* 90(6): 397-400, English translation and certificate of translation included, 4 pages.

Yamamoto, T. and Miyagawa, F. (1978) "Photoradiation therapy, phytochlorin and visible light" *Prevention and Detection of Cancer, Part 1, Prevention. vol. 2, Etiology-Prevention Methods* Proceedings of the Third International Symposium on Detection and Prevention of Cancer held Apr. 26, 1976 in New York, NY, 1(2):1789-1802.

Aiello, L.P. et al. (1998). "Diabetic Retinopathy," *Diabetes Care* 21:143-156.

Birchler, M. et al. (1999). "Selective Targeting and Photocoagulation of Ocular Angiogenesis Mediated by a Phage-Derived Human Antibody Fragment," *Nature Biotech.* 17:984-988.

Casalini, P. et al. (1997). "Tumor Pretargeting: Role of Avidin/Streptavidin on Monoclonal Antibody Internalization," *J. Nuclear Med.* 38(9):1378-1381.

Chen, Y.R. et al. (1998). "Bilateral Choroidal Metastases as the Initial Presentation of a Small Breast Carcinoma: A Case Report," *Chin Med J.* (Taipei) 61(2):99-103.

Devoisselle, J.M. et al. (1995). "Effect of Indocyanin Green Formulation on Blood Clearance and in Vivo Flourescence Kinetic Profile of Skin," *SPIE* 2627:100-108.

Dillon, J. et al.(1988). "In Vitro and In Vivo Protection Against Phototoxic Side Effects of Photodynamic Therapy by Radioprotective Agents WR-2721 and WR-77913," *Photochemistry and Photobiology* 48(2):235-238.

Eliceiri, B.P. and Cheresh, D. A. (1999). "The Role of αv Integrins During Angiogenesis: Insights Into Potential Mechanisms of Action and Clinical Development," *The Journal of Clinical Investigation* 103(9):1227-1030.

Ferrara, N. (1999). "Vascular Endothelial Growth Factor: Molecular and Biological Aspects," *Curr Top Microbiol Immunol.* 237:1-30.

Fisher, W.G., et al. (1997). "Simultaneous Two-Photon Activation of Type-I Photodynamic Therapy Agents," *Photochemistry and Photobiology* 66(2):141-155.

Kreimer-Birnbaum, M. (1989). "Modified Porphyrins, Chlorins, Phthalocyanines, and Purpurins: Second-Generation Photosensitizers for Photodynamic Therapy," *Sem .in Hematol.* 26(2):157-73.

Maniotis, A.J. et al. (1999). "Vascular Channel Formation by Human Melanoma Cells in Vivo and in Vitro: Vasculogenic Mimicry," *American Journal of Pathology* 155(3):739-52.

Mew, D. et al. (1983). "Photoimmunotherapy: Treatment of Animal Tumors with Tumor-Specific Monoclonal Antibody-Hematoporphyrin Conjugates,"*J. of Immunol.* 130(3):1473-1477.

\* cited by examiner

PHOTODYNAMIC THERAPY TREATMENT FOR EYE DISEASE

RELATED APPLICATIONS

This application is a Continuation-in-part of U.S. patent application Ser. No. 09/760,362, filed Jan. 12, 2001 now abandoned, which further claims the benefit of U.S. Provisional Patent Application No. 60/175,689, filed Jan. 12, 2000 (now abandoned).

All patent applications noted above are incorporated by reference in their entirety to provide for continuity of disclosure.

FEDERALLY SPONSORED RESEARCH OR DEVELOPMENT

Not Applicable

MICROFICHE/COPYRIGHT REFERENCE

Not Applicable

TECHNICAL FIELD

This invention relates generally to the field of medicine and pharmacotherapeutics with photosensitizing agents or other energy activated agents. Specifically, this invention relates to kits and methods useful for the treatment of neovascular diseases of the eye. The invention involves the site specific delivery to a neovasculature target tissue of a therapeutically effective amount of a photosensitizing agent that is activated by a relatively low fluence rate of light over a prolonged period of time.

BACKGROUND OF THE INVENTION

Neovascular diseases of the eye include diabetic retinopathy, age-related macular degeneration and neovasculature growth induced by angiogenic factors or resulting from tumor cells, themselves. Diabetic retinopathy is characterized by a number and variety of microvascular changes which can result ultimately in adverse visual changes and vision loss. In many cases the microvascular changes are due to or associated with upregulation of angiogenesis receptors and factors of ligands which lead to new vessel formation, changes in vascular permeability, and possibly other alterations in vessel morphology. These changes may lead to hemorrhage, edema, ischemia, and other problems resulting in vision dysfunction (see: Aiello et al., Diabetes Care, 21:143-156, 1998).

Treatments for the various forms of, and problems associated with, diabetic retinopathy include laser photocoagulation, vitrectomy, cryotherapy, and membranotomy. All of these clinical therapies and procedures are associated with problems and side effects. For example, the side effects and complications related to panretinal laser photocoagulation, the most common present treatment for diabetic retinopathy, include: decreased visual acuity, increased macular edema, transient pain, exudative retinal detachment, and inadvertent foveolar burns.

Age-related macular degeneration ("AMD") is the leading cause of blindness in the United States among individuals 65 or older. One form of AMD is characterized by formation of choroidal neovessels which can lead to a number of pathologic conditions resulting in visual dysfunction and loss. As with diabetic retinopathy, angiogenesis plays a key role in the formation of these neovessels. The proliferation of choroidal neovessels associated with AMD can contribute to irreversible damage of photoreceptors. Thus, current treatment of AMD, like that of diabetic retinopathy, involves the use of laser photocoagulation. However, because photocoagulation relies upon the gross thermal destruction of the choroidal neovascular tissue, damage to the retina and surrounding choroidal tissue often results. Furthermore, recurrences after photocoagulation therapy are common. (see: Schmidt-Erfurth et al., Greafe's Arch Clin Exp Opthamol, 236:365-374, 1998).

As an alternative to photocoagulation, photodynamic therapy has been proposed as a means of treating this form of AMD (see: Strong et al., "Vision through photodynamic therapy of the eye," U.S. Pat. Nos. 5,756,541 and 5,910,510; and Mori et al., "Photochemotherapeutical obstruction of newly-formed blood vessels," U.S. Pat. No. 5,633,275). Photodynamic therapy ("PDT"), as taught in this prior art, is a two-step treatment process. PDT is performed by first administering a photosensitive compound systemically or topically, followed by illumination of the treatment site at a wavelength or waveband of light from a laser which closely matches the absorption spectra of the photosensitizer. In doing so, singlet oxygen and other reactive species are generated leading to a number of biological effects resulting in damage to the endothelial membranes and ultimately to clotting of the neovasculature.

Although this form of PDT represents an improvement over photocoagulation, clinical experience has established that the therapy must be repeated on a regular basis, typically every 3 months due to regrowth of the vessels (see: Schmidt-Erfurth et al.). The regrowth is believed to be due to upregulation of angiogenic factors and/or receptors secondary to the relative ischemia caused by the PDT treatment as outlined in the prior art. Clearly there is a need for a therapy which reduces the number of treatments which probably need to be performed for the rest of the patient's life.

In addition to neovascular tissue formation associated with diabetic retinopathy and age-related macular degeneration, the growth of new blood vessels are also associated with tumor formation in the eye, which results from two mechanisms: the stimulated growth of endothelial cells of existing blood vessels through angiogenesis; and a newly discovered vasculature resulting from highly malignant uveal melanomas, which develop in the eye, are full of networks of blood channels made by the melanoma cells themselves (Maniotis et al., American Journal of Pathology 155(3):739-52 (1999)). It may be that anti-angiogenic agents are ineffective in the treatment of such neovasculature arising not from endothelial cells, but from tumor cells such as those of malignant uveal melanomas.

Furthermore, because current PDT methods involve the systemic administration of untargeted photosensitive compounds or photosensitizers, the required dosages are relatively high which can lead to skin photosensitivity. The accumulation of photosensitizers in the skin is a property of all systemically administered sensitizers in clinical use. For example, clinically useful porphyrins such as Photophrin.RTM. (QLT, Ltd. brand of sodium porfimer) are associated with photosensitivity lasting up to 6 weeks. Purlytin.RTM., which is a purpurin, and Foscan.RTM., a chlorin, sensitize the skin for several weeks. Indeed, efforts have been made to develop photoprotectants to reduce skin photosensitivity (see: Dillon et al., Photochemistry and Photobiology, 48(2): 235-238, 1988; and Sigdestad et al., British J. of Cancer, 74:S89-S92, 1996). In fact, PDT protocols involving systemic administration of photosensitizer require that the patient avoid sunlight and bright indoor light to reduce the chance of skin phototoxic reactions.

While there are reports in the scientific literature describing the use of ligand-receptor binding pairs, the literature is primarily drawn to the treatment of malignant tumor cells. There are a few reports that address the treatment of eye-related neovascular diseases such as diabetic retinopathy and AMD. However, either these reports fail to disclose the use of PDT at all or these reports fail to teach the use of such methods in conjunction with the targeting of blood vessels (see, for example: Savitsky et al., SPIE, 3191:343-353, 1997; Ruebner et al., SPIE, 2625: 328-332, 1996; Reno et al., U.S. Pat. No. 5,630,996; Casalini et al., J. Nuclear Med., 38(9):1378-1381, 1997; Griffiths, U.S. Pat. No. 5,482,698; and Mew et al., J. of Immunol., 130(3): 1473-1477, 1983). It should be noted that even though Strong et al. U.S. Pat. Nos. 5,756,541 and 5,910,510 suggest that a photoactive agent may be coupled to a specific binding ligand which may bind to a specific surface component of the target ocular tissue, there is little guidance provided to suggest appropriate ligands effective in such PDT methods.

Regarding light sources for PDT, high powered lasers are usually employed in order to shorten the procedure time (see: Strong et al., U.S. Pat. Nos. 5,756,541 and 5,910,510; and Mori et al., U.S. Pat. No. 5,633,275; see more generally, W. G. Fisher, et al., Photochemistry and Photobiology, 66(2):141-155, 1997).

However, the present art lacks an effective method of treating neovasculature diseases of the eye using a PDT methodology, which reduces damage to collateral or healthy tissue and which does not expose the tissue of the eye to intense laser light. The present art further teaches the need for recurrent treatment, the need for which is thought to arise, as discussed above, due to upregulation of angiogenic factors and/or receptors secondary to the relative ischemia caused by the PDT treatment as outlined in the prior art. Clearly there is a need for a therapy which reduces the number of treatments which probably need to be performed for the rest of the patient's life.

Citation of the above documents is not intended as an admission of any of the foregoing is pertinent prior art. All statements as to the date representation as to the contents of these documents is based on the information available to the applicants and does not constitute any admission as to the correctness of the dates or contents of these documents. Further, all documents referred to throughout this application are incorporated in their entirety by reference herein.

BRIEF SUMMARY OF THE INVENTION

The present invention describes methods to treat neovascular disease of the eye based on the precise targeting of photosensitive compounds to target tissue and the activation of these targeted photosensitizer compounds by subsequently administering to the subject non-coherent (non-laser) or coherent (laser) light of a relative low fluence rate over a prolonged period of time.

The present invention further discloses the selective binding of the photosensitizing agent to specific receptors and/or antigens present on abnormal endothelium or to specific ligands and/or antibodies which are themselves bindable to endothelial receptors and antigens. This targeting scheme decreases the amount of sensitizing drug required for effective therapy, which in turn reduces the fluence rate or light irradiation needed for effective photoactivation. As a result, the disclosed method achieves maximal dosage to abnormal endothelium and minimal side effects or collateral tissue damage.

Additionally, the present disclosure teaches the unexpected use of a low power non-coherent light source utilized for longer than about 4 minutes. This teaches away from the use of a high powered, brief exposure using laser light, results in fuller, more efficient activation of the bound photosensitizers, and enables a high therapeutic index using a low dose drug. Moreover, a low power non-coherent light source is relatively inexpensive and simpler to use. Finally, because the present invention teaches photoactivation with a non-coherent, broadband light source, different types of photosensitizers can be activated with a single light source.

Due to the highly specific nature of the photosensitizer uptake, excess light or light falling on nonpathologic areas causes no unwanted photoactivation. Therefore, a region of the retina or macular with diffuse abnormalities can be safely treated without damaging intervening normal eye structures. In addition, eye movement by the patient during treatment, which can result in the further exposure to light of normal eye structures, is harmless. Thus, the use of highly targeted photosensitizers allows the delivery of light in a diffuse fashion and over a prolonged illumination period. In fact, one embodiment of the invention is the use of ambient light to activate the photosensitized neovascular tissue.

Further the binding of the photosensitizer/ligand conjugate to the endothelial receptor, as taught by the present invention, causes blockage and/or down regulation of the receptor which further inhibits neovessel formation and subsequent regrowth of neovasculature, which generally results from more traditional methods of PDT. Similarly, the use of a photosensitizer/receptor conjugate would serve to bind circulating ligands also inhibiting neovessel formation. This added benefit of the present invention operates independently of the light-activated vessel occlusion described above.

An embodiment of the present invention is drawn to a method for photodynamic therapy ("PDT") of neovascular disease of the eye comprising: administering to the subject a therapeutically effective amount of a photosensitizing compound, where the photosensitizing compound selectively binds to the target abnormal endothelium that lines or composes the neovasculature target tissue. This step is followed by illuminating the neovasculature tissue with light at a wavelength or waveband absorbed by the targeted photosensitizing compound where the light is provided by a non-laser light source, and for a period of time sufficient to activate the photosensitizing compound thereby causing damage to the neovasculature target tissue. In this embodiment of the present invention, the targeted photosensitizing compound is cleared from non-target tissues of the subject prior to irradiation.

A preferred embodiment of the present invention is drawn to a method for PDT of neovascular disease of the eye as described above, wherein the neovascular target tissue is present in the retina, choroid or both of a subject diagnosed with diabetic retinopathy or age-related macular degeneration ("AMD"). A further preferred embodiment of this invention provides a method for PDT of neovascular tissue associated with tumor formation in the eye, and more specifically neovascular tissue resulting from angiogenesis or growth factors elicited by tumors, such as malignant uveal melanomas.

A more preferred embodiment of the present invention is drawn to a method of PDT of neovascular disease of the eye as described above, wherein the targeted photosensitizing compound is bound to a first component of a bindable pair and wherein the second component of the bindable pair is selected from the group consisting of: receptor present on abnormal endothelium; ligand bindable to receptor present on abnormal endothelium; antigen present on abnormal endothelium; and antibody bindable to antigen present on abnormal endothelium.

Yet another preferred embodiment contemplates a method of PDT of neovascular disease of the eye as described above, where the ligand is selected from a group consisting of: VEGF; VEGF receptor; and .alpha.-3, .beta.-3 integrin receptor. A further preferred embodiment provides a method of PDT of neovascular disease of the eye, where the ligand comprises an antibody specific or having a high degree of affinity for the extra-domain B (or ED-B) of fibronectin. An even more preferred embodiment is drawn to the ligand discussed above, which is a complete or functional bindable fragment of a human antibody, such as L19 or its equivalent (see: Birchler et al., Selective targeting and photocoagulation of ocular angiogenesis mediated by a phage-derived human antibody fragment, Nature Biotech. 17:984 (1999)).

Another preferred embodiment of the present invention is drawn to a method of PDT of neovascular disease of the eye as described above, where the targeted photosensitizing compound is bound to a receptor composition that mimics a receptor present on abnormal endothelium.

Another preferred embodiment of the present invention is drawn to a method of PDT of neovascular disease of the eye as described above, where the targeted photosensitizing compound is bound to a bi-specific antibody construct that further comprises both a ligand component and a receptor component.

A still further embodiment of the present invention is drawn to a method of PDT of neovascular disease of the eye as described above, where the targeted and bound photosensitizing compound is incorporated into a liposomal preparation.

The invention also provides kits comprising any of the components that are used in PDT of neovascular disease as taught herein and instructions (such as an instruction sheet or computer disk) that teach the methods described herein.

The invention also provides methods of teaching a person to conduct treatments of neovascular disease, where the methods comprise instructing a person to conduct the PDT methods described herein.

BRIEF DESCRIPTION OF SEVERAL VIEWS OF THE DRAWINGS

FIG. 1 further illustrates free circulating photosensitizing ligand construct 140.

DETAILED DESCRIPTION OF THE INVENTION

This invention provides methods for treating neovascular disease of the eye by the specific and selective binding of a photosensitizing compound to the abnormal endothelium that lines or composes the neovasculature target tissue. This method comprises illuminating the photosensitized target tissue with light for a period of time sufficient to activate the bound photosensitizing compound thereby causing damage to the neovasculature target tissue.

Specifically, the present invention is based on the precise targeting of photosensitizing compounds to specific target receptors and/or antigens present on abnormal endothelium or to specific ligands and/or antibodies which are themselves bindable to endothelial receptors and antigens, and to the method of activation of the bound and targeted photosensitizing compounds by subsequently administering to the target tissue light of a relatively low fluence rate over a prolonged period of time. The disclosed method achieves maximal damage to abnormal endothelium with minimal side effects or collateral tissue damage.

Terms as used herein are based upon their art recognized meaning and from the present disclosure should be clearly understood by the ordinary skilled artisan. For sake of clarity, terms may also have particular meaning as would be clear from their use in context.

Further, as used herein, "target tissues" are those tissues that are intended to be impaired or destroyed by this treatment method. Photosensitizing compounds bind to these target tissues; then when sufficient radiation is applied, these tissues are impaired or destroyed.

"Non-target tissues" are all the tissues of the eye which are not intended to be impaired or destroyed by the treatment method. These non-target tissues include but are not limited to healthy blood cells, and other normal tissue of the retina and choroid, not otherwise identified to be targeted.

"Photosensitizing compound" is a chemical compound which homes to one or more types of selected target cells and, when contacted by radiation, absorbs the light, which results in impairment or destruction of the target cells. Virtually any chemical compound that homes to a selected target and absorbs light may be used in this invention. Preferably, the chemical compound is nontoxic to the subject to which it is administered or is capable of being formulated in a nontoxic composition. Preferably, the chemical compound in its photodegraded form is also nontoxic. A comprehensive listing of photosensitive chemicals may be found in Kreimer-Birnbaum, Sem. Hematol. 26:157-73, 1989. Photosensitive compounds include, but are not limited to, chlorins, bacteriochlorophylls, phthalocyanines, porphyrins, purpurins, merocyanines psoralens, benzoporphyrin derivatives (BPD) and porfimer sodium and pro-drugs such as delta.-aminolevulinic acid, which can produce drugs such as protoporphyrin. Other compounds include indocyanine green (ICG); methylene blue; toluidine blue; texaphyrins; and any other agent that absorbs light in a range of 500 nm-1100 nm.

"Illumination" as used herein includes all wave lengths and wavebands. Preferably, the illumination wave length or waveband is selected to match wave length(s) or wavebands which excite the photosensitive compound. Even more preferably, the radiation wave length or waveband matches the excitation wave length or waveband of the photosensitive compound and has low absorption by the non-target tissues of the eye, and the rest of the subject, including blood proteins.

The irradiation by illumination is further defined in this invention by its coherence (laser) or non-coherence (non-laser), as well as intensity, duration, and timing with respect to dosing using the photosensitizing compound. The intensity or fluence rate must be sufficient for the light to reach the target tissue. The duration or total fluence dose must be sufficient to photoactivate enough photosensitizing compound to act on the neovasculature target tissue. Both intensity and duration must be limited to avoid overtreating the subject. Timing with respect to dosing with the photosensitizing compound is important because 1) the administered photosensitizing compound requires some time to home in on neovasculature target tissue and 2) the blood level of many photosensitizing compounds decreases with time.

Briefly, the photosensitizing compound is generally administered to the subject before the neovasculature target tissue is subjected to illumination.

Preferred photosensitizing compounds include, but are not limited to, chlorins, bacteriochlorophylls, phthalocyanines, porphyrins, purpurins, merocyanines, psoralens and pro-drugs such as .delta.-aminolevulinic acid, which can produce drugs such as protoporphyrin. More preferred are: methylene blue; toluidine blue; texaphyrins; and any other agent that absorbs light in a range of 600 nm-1100 nm. Most preferred is indocyanine green (for example, see WO 92/00106 (Raven et al.); WO 97/31582 (Abels et al.) and Devoisselle et al., SPIE 2627:100-108, 1995). Additional photosensitizing compounds, include: pyropheophorbide compounds (see: U.S. Pat. No. 5,459,159); bacteriochlorophyll derivatives (see: U.S. Pat. No. 5,955,585); and Alkyl ether analogs of chlorins (see: U.S. Pat. No. 5,952,366).

Any one or combination of these or other photosensitizing compounds may be supplied in a kit of this invention along with instructions on conducting any of the methods disclosed herein. Instructions may be in any tangible form, such as printed paper, a computer disk that instructs a person how to conduct the method, a video cassette containing instructions on how to conduct the method, or computer memory that receives data from a remote location and illustrates or otherwise provides the instructions to a person (such as over the Internet). A person may be instructed in how to use the kit using any of the instructions above or by receiving instructions in a classroom or in the course of treating a patient using any of the methods disclosed herein, for example.

Figure 1:
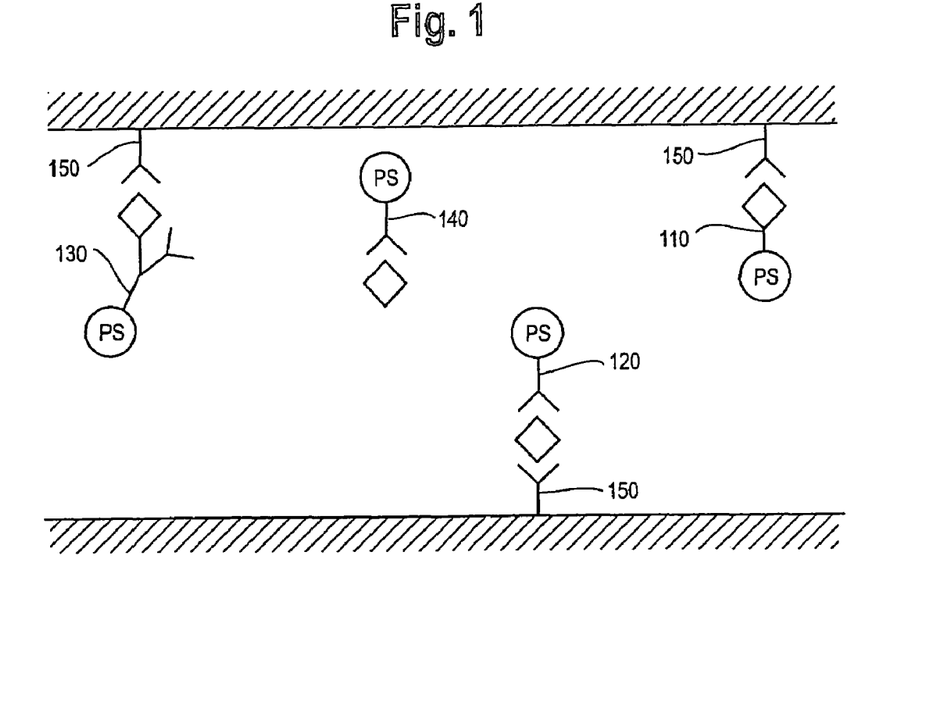
FIG. 1 illustrates three types of photosensitizing compounds bound to receptors 150 on an abnormal blood vessal wall. One is bound via a ligand construct 110, another is bound via a receptor construct 120, and the third is bound via a bispecific antibody construct 130.

The photosensitizing compound is administered orally, intravenously by injection, or via the intraocular route. The photosensitizing compound can be conjugated to various antibodies, antibody fragments, and other molecules and compounds capable of binding to the endothelium of neovessels. The specific ligands reactive with the target endothelium include antibodies and antibody fragments that bind to abnormal or upregulated vascular endothelial receptors such as the VEGF receptors and .alpha.-3, .alpha.-3 integrins (see: Ferrara, Curr Top Microbiol Immunol, 237: 1-30, 1999; Elicieri and Cheresh, The Journal of Clinical Investigation, 103:1227-30, 1999; Smith et al., Br J Opthamol, 83:486-494, 1999). Also, the antibody can be drawn to and have affinity to bind to the extra-domain B (or ED-B) of fibronectin. Such antibodies, include a complete or functional bindable fragment of a human antibody, such as L19 or its equivalent (see: Birchler et al., Selective targeting and photocoagulation of ocular angiogenesis mediated by phage-derived human antibody fragment, Nature Biotech. 17:984 (1999)). The ligand can be any molecule or compound that binds to a endothelial receptor found on an abnormal blood vessel wall. Preferably the ligand binds selectively to receptors which are mainly or only found on the abnormal blood vessel wall. FIG. 1, for example, illustrates an embodiment in which ligand construct 110 is bound to a receptor 150 on abnormal blood vessel wall, in accordance with the present technology.

Another embodiment of the present invention involves the use of a photosensitizing compound bound to a receptor-type molecule or compound. The receptor mimics the type of receptors found on the endothelium of abnormal vessel walls. Preferably the receptor mimic binds ligands, such VEGF, that are found to be elevated in concentration or are not normally present due to the abnormal conditions relating to the abnormal blood vessel formation. FIG. 1, for example, illustrates illustrates an embodiment in which receptor construct 120 is bound to a receptor 150 on abnormal blood vessel wall, in accordance with the present technology. An additional embodiment involves the use of a bispecific antibody construct that is a combination ligand and receptor type molecule or compound that is bound to a photosensitizing compound. The bispecific nature of this construct allows binding of either an abnormal endothelial receptor or an abnormal ligand or abnormally elevated concentration of ligand. Again, FIG. 1, for example, illustrates an embodiment in which bispecific antibody construct 130 is bound to a receptor 150 on abnormal blood vessel wall, in accordance with the present technology.

Figure 2:
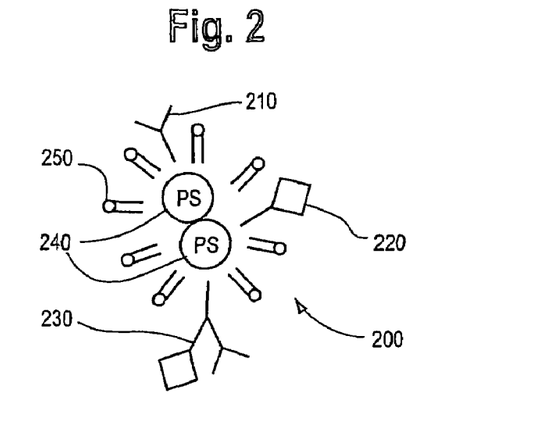
FIG. 2 illustrates photosensitizing compounds 240 incorporated into a liposomal preparation 200 having liposomes 250, that includes a ligand construct 220, a receptor construct 210, and a bispecific antibody construct 230.

Alternatively, the photosensitizing compound can be packaged into liposomes and the ligand, receptor, or bispecific construct incorporated or attached to the liposome to serve as a further means of targeting. In each of the above embodiments, preferably more than one photosensitizing compound is attached to the targeting moiety. FIG. 2, for example, illustrates an embodiment in which photosensitizing compounds 240 are incorporated into a liposomal preparation 200 that includes liposomes 250, a ligand construct 220, a receptor construct 210, and a bispecific antibody construct 230, in accordance with the present technology.

The technique of constructing bispecific antibodies, the techniques and methods of linking photosensitizers to targeting agents, and the techniques of producing targeted liposomes are well known in the art. For example, useful reviews of such techniques are provided by Yatvin et al., U.S. Pat. No. 5,827,819 (1998) and Jansen, et al. U.S. Pat. No. 5,869,457 (1999).

The bound photosensitizing compound can be administered in a dry formulation, such as pills, capsules, suppositories or patches. The compound also may be administered in a liquid formulation, either alone with water, or with pharmaceutically acceptable excipients, such as are disclosed in Remington's Pharmaceutical Sciences. The liquid formulation also can be a suspension or an emulsion. In particular, liposomal or lipophilic formulations are desirable. If suspensions or emulsions are utilized, suitable excipients include water, saline, dextrose, glycerol, and the like. These compositions may contain minor amounts of nontoxic auxiliary substances such as wetting or emulsifying agents, antioxidants, pH buffering agents, and the like.

The dose of photosensitizing compound can be determined clinically and will be the lowest dose that saturated the available binding sites. Depending on the photosensitizing compound used, an equivalent optimal therapeutic level will have to be established. A certain length of time is allowed to pass for the circulating or locally delivered photosensitizer to be taken up by the endothelium of the neovessels. The unbound photosensitizer is cleared from the circulation during this waiting period. The waiting period will be determined clinically and may vary from compound to compound.

Figure 3:
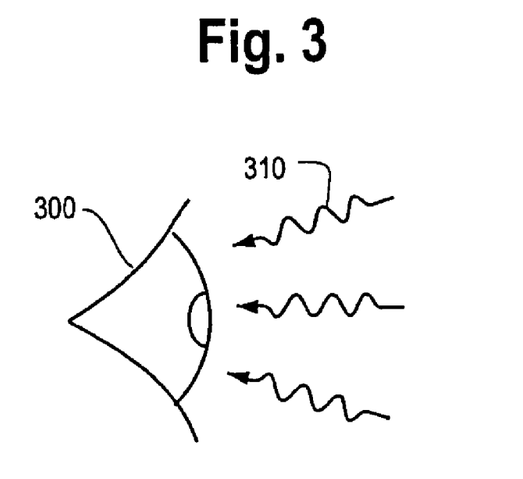
FIG. 3 shows an eye 300 subjected to ambient light 310.
Figure 4:
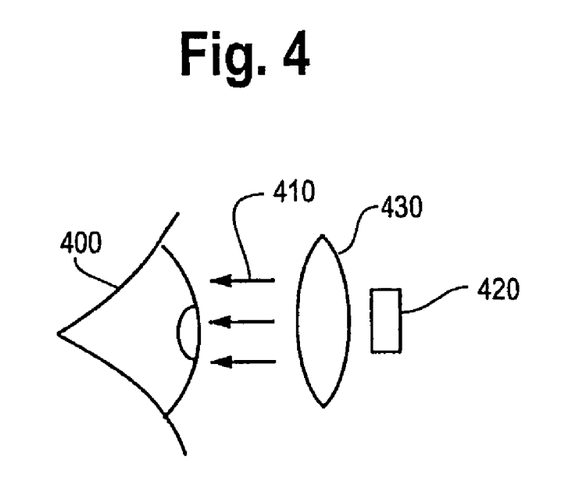
FIG. 4 shows eye 400 subjected to collimated LED light 410, wherein LED light from LED light source 420 is collimated by a focusing lens 430.
Figure 5:
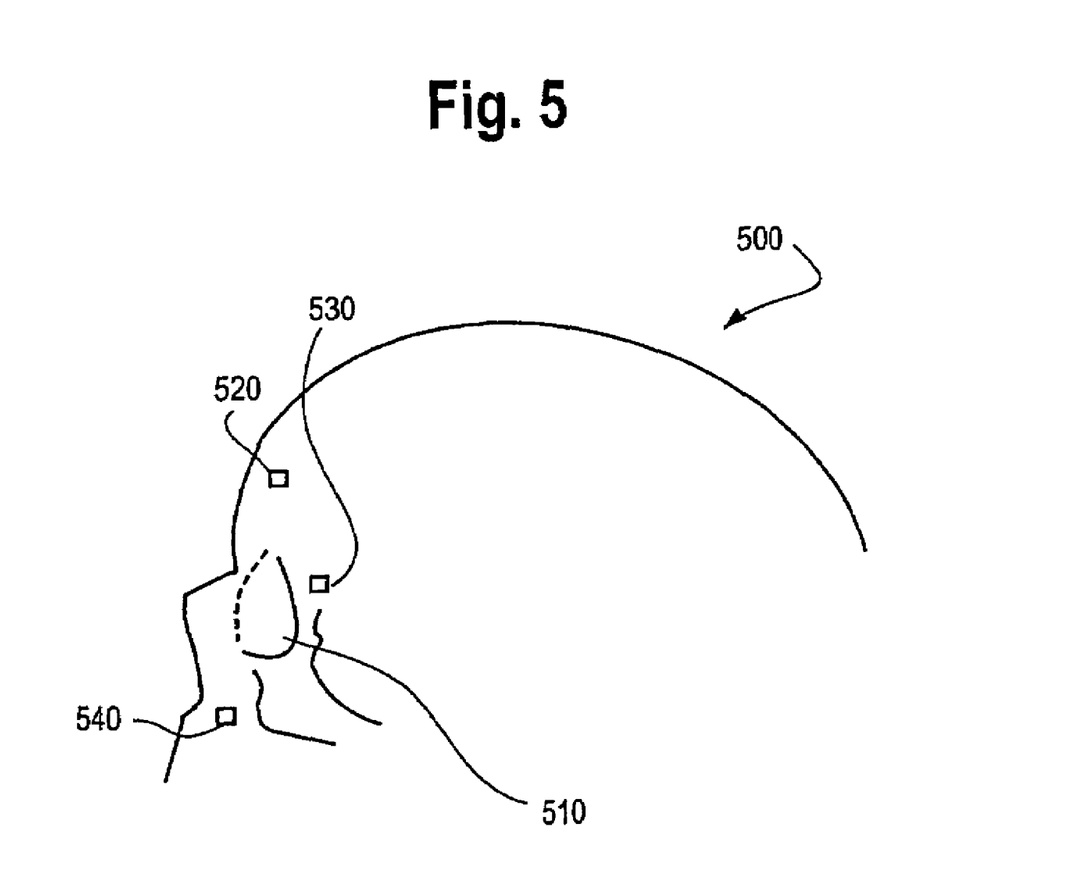
FIG. 5 shows a lateral view of skull 500 (partial) having eye socket 510, with locations for LED light delivery indicated at the superior orbital location 520, the lateral orbital location 530, and the inferior orbital location 540.

At the conclusion of this waiting period, a non-laser light source is used to activate the bound drug, although a laser light source may be used. For example, FIG. 3 shows an eye 300 subjected to ambient light 310. Ambient light 310 can strike abnormal and normal blood vessels in eye 300. As another example, FIG. 4 shows eye 400 subjected to collimated LED light 410, where LED light from LED light source 420 is collimated by a focusing lens 430. The collimated LED light 410 can be delivered to abnormal and normal vessels of eye 400. The spot size illuminating the retina or choroid is determined by the location and dimension of the pathologic region to be treated. Examples of treatment locations are shown in FIG. 5, which illustrates a lateral view of skull 500 (partial) having eye socket 510, with locations for LED light delivery indicated at the superior orbital location 520, the lateral orbital location 530, and the inferior orbital location 540. The light can be transcutaneously delivered to any, or all, of the indicated tratement locations through the skin, soft tissue and orbital walls of the patient being treated. The duration of illumination period will be determined empirically, but is preferably a total or cumulative period of time between about 4 minutes and 72 hours. More preferably, the illumination period is between about 60 minutes and 148 hours. Most preferably, the illumination period is between about 2 hrs and 24 hours.

Preferably, the total fluence or energy of the light used for irradiating, as measured in Joules, is between about 30 Joules and about 25,000 Joules; more preferably, between about 100 Joules and about 20,000 Joules; and most preferably, between about 500 Joules and about 10,000 Joules. Light having a waveband corresponding at least in part with the characteristic light absorption waveband of said photosensitizing agent is used for irradiating the target tissue.

The intensity or power of the light used is measured in watts, with each Joule equal to one watt-sec. Therefore, the intensity of the light used for irradiating in the present invention may be substantially less than 500 mW/cm.sup.2. Since the total fluence or amount of energy of the light in Joules is divided by the duration of total exposure time in seconds, the longer the amount of time the target is exposed to the irradiation, the greater the amount of total energy or fluence may be used without increasing the amount of the intensity of the light used. The present invention employs an amount of total fluence of irradiation that is sufficiently high to activate the photosensitizing agent, as applicable, with a concomitant reduction in the intensity of light and collateral or non-target specific tissue damage.

While not wishing to be limited by a theory, the inventor proposes that a targeted photosensitizing compound can be substantially and selectively photoactivated in the neovasculature target tissue within a therapeutically reasonable period of time and without excess toxicity or collateral damage to non-target tissues. A relatively low fluence can be used for a relatively long period of time in order to fully photoactivate the drug in order to insure adequate closure of the neovessels and vessel abnormalities.

Having now generally described the invention, the same will be more readily understood through reference to the following examples which are provided by way of illustration, and are not intended to be limiting of the present invention, unless specified.

EXAMPLES

Example 1

Treatment of Choroidal Neovasculature Lesions

A subject with choroidal neovascularization (CNV) from age-related macular generation is assessed using standard visual acuity testing, ophthalmic examination, color photographs and fluorescein angiograms (see Miller et al., Ach. Ophthal. Vol 117:1161-1173 (1999)).

A photosensitizing agent, verteporfin, is conjugated using generally recognized methods in the art to a bindable fragment of the L19 antibody demonstrating high affinity to the ED-B of fibronectin (Birchler et al., Nature Biotech. 17:984 (1999)). A therapeutically effective amount of the photosensitizing agent conjugate, approximately 5 mg/m.sup.2, is administered intravenously to the subject.

Following a period of approximately 1 hour, to permit the non-specifically bound photosensitizing agent conjugate to clear from collateral tissues, the subject is irradiated in one or more sessions for a total period of 10 minutes with 400 mW/cm.sup.2 of collimated LED light having a wavelength of 690 nm. This represents a total fluence of 240 Joules/cm.sup.2.

The entire lesion is treated with a single spot of the size as determined from a pretreatment angiogram. A margin of 300-500 mu.m may be added to ensure complete coverage of the lesion. A green non-activating observation light beam may be used for real-time observation and aiming during PDT.

Screening examinations may be performed during the first week immediately before treatment. Visual acuity is measured by standard refraction protocol using EDTRS criteria. A slit-lamp and a complete opthalmoscopic exam is performed. Optic discs and maculae of both eyes are document by stereo color photography. Stereo fluorescein angiography is performed with 10% sodium fluorescein. Frames are taken according to MPS standards. The photodynamic effects are monitored after 1, 4, and 12 weeks by means of visual acuity, opthalmoscopy, fundus photography and stereo angiography. Angiograms are evaluated for angiographic occlusion and leakage after PDT.

Example 2

Treatment of Retinal Neovasculature Lesions

According to Example 1, a lipsomal benzoporphyrin derivative is conjugated to VEGF for use as a photosensitizer. The drug dose of 10 mg/m.sup.2 is administered to a subject with neovascular lesions in the retina of the eye via intravenous infusion over 10 minutes. The subject waits for a period of 6 hours to permit clearance from the tissues of non-specifically bound photosensitizing conjugate before illumination therapy is administered.

With the photosensitizer specifically localized to the retinal neovasculature lesions comprising VEGF receptor on the surface of the cells of the lesion, the subject is exposed to non-coherent light from a low power non-coherent broadband light source emitting at 690 nm. This illumination provides a radiant exposure of no more than 500 mW/cm-.sup.2 for a period of approximately 20 minutes in one or more sessions producing a total fluence of illumination of about 600 Joules/cm.sup.2. Alternatively, coherent or laser light could be similarly employed. Photosensitization is performed with dilated pupils and topical anesthesia using a contact lens.

The entire lesion is treated with a single spot of the size as determined from a pretreatment angiogram. A margin of 300-500 mu.m is added to ensure complete coverage of the lesion. The green non-activating observation light beam is used for real-time observation and aiming during PDT. Screening examinations and visual acuity as disclosed in Example 1 is performed.

Example 3

Treatment of Vascular Tumors of the Eye

Integrin .alpha.v.beta.3 integrin is expressed by vascular cells during angiogenesis and vascular remodeling and is highly expressed by endothelial cells undergoing angiogenesis in tumors. See Eliceiri, B. P. et al., J. Clin. Invest (1999) 103(9):1227-1230. Antibody elicited to .alpha.v.beta.3, such as LM609 (Vitaxin; Eliceiri et al.) is conjugated to a texaphyrin photosensitizing agent in a liposomal formulation. A drug dose of 25 mg/m.sup.2 is administered via intravenous infusion over 10 min. The photosensitizer localizes to the neovasculature lesions. The pupils are dilated to allow ambient light enter for photosensitization. Therefore, no slit lamp is needed for photosensitization and the subject may continue every day activities while receiving PDT. The ambient light is used to photoactivate the photosensitizing agent for a total exposure time of 24 hours.

Screening examinations and visual acuity as disclosed in Example 1 is performed.

Example 4

Treatment Choroidal Tumor of the Eye

Most ocular tumors metastasize from systemic origins in breast carcinoma in females, and bronchial carcinoma in males (Chen Y R, et al. Bilateral choroidal metastases as the initial presentation of a small breast carcinoma: a case report, Chung Hua I Hsueh Tsa Chih (Taipei); 61(2):99-103 1998). Antibody elicited to carcinoembryonic antigen (CEA), which is associated with the choroidal tumor, is conjugated to a benzoporphyrin derivative photosensitizing agent in a liposomal formulation. A drug dose of 10 mg/m.sup.2 is administered via intravenous infusion over 10 min.

Additionally, the patient is administered the anti-.alpha.v-.beta.3 antibody-texaphyrin conjugate at a drug dose of 25 mg/m.sup.2 as provided in Example 3

After the texaphyrin photosensitizer conjugate localizes to the neovasculature lesion and the benzoporphyrin-anti-CEA conjugate localizes to the CEA tumor antigens, a period of 6 hours is permitted to pass to permit the unbound or non-specifically bound photosensitizer conjugates to clear from the lesions.

A low power non-coherent broadband light source emitting at 690 nm is used as described in Example 2. The radiant exposure of 250 mW/cm.sup.2 is employed for approximately 1 hour over the course of one or more sessions to provide a total fluence of 900 J/cm.sup.2. Photosensitization is performed with dilated pupils and topical anesthesia using a contact lens. The entire lesion is treated with a single spot of the size as determined form pretreatment angiogram. A margin of 300-500 mu.m is added to ensure complete coverage of the lesion. A green non-activating observation light beam is used for real-time observation and aiming during PDT. Screening examinations and visual acuity as disclosed in Example 1 is performed.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention claimed is:

1. A method of treating neovascular disease of the eye, comprising:
   administering a conjugate to target neovascular tissue of the eye comprising:
   a photosensitizing compound selected from the group consisting of chlorines, bacteriochlorophylls, phthalocyanines, porphyrins, purpurins, merocyanines, psoralens, porfimer sodium, delta-aminolevulinic acid protoporphyrin, indocyanine green, benzoporphyrin, methylene blue, toluidine blue, texaphyrins, pyropheophorbide compounds, and verteporfin; and
   a targeting moiety that selectively binds to abnormal endothelium, wherein the targeting moiety consists of an antibody or an antibody fragment thereof that binds to a VEGF receptor;
   allowing sufficient time for the conjugate to clear from non-targeted tissue of the eye; and
   illuminating the eye with a light having a wave length or waveband absorbed by the targeted photosensitizing compound to activate the photosensitizing compound, and
   wherein the light has a combination of an intensity of light of less than 500 mW/cm$^2$ and a duration of illumination of about 4 minutes to produce a total fluence of light irradiation from between about 30 J/cm$^2$ to about 25,000 J/cm$^2$ which destroys the targeted neovascular tissue while the non-targeted tissue remains undamaged.

2. The method of claim 1, wherein the sufficient time for the conjugate to clear from the non-targeted tissue is about 24 hours or less.

3. The method of treating neovascular disease of the eye of claim 1, wherein the method is performed one time or multiple times in the eye.

4. The method of claim 1, wherein the light is non-coherent light.

5. The method of claim 1, wherein the light is coherent light.

6. The method of claim 1, wherein the neovascular tissue is present in retina, choroids or both.

7. The method of claim 1, wherein the total fluence of light irradiation from between about 30 J/cm$^2$ to about 10,000 j/cm$^2$.

8. The method of claim 1, wherein the total fluence of light irradiation from between about 30 J/cm$^2$ to about 900 J/cm$^2$.

9. The method of claim 1, wherein the eye is illuminated with a light having a wave length or waveband that matches the excitation wave length or waveband of the targeted photosensitizing compound to activate the photosensitizing compound.

10. The method of claim 1, wherein the neovascular disease is diabetic retinopathy.

11. The method of claim 1, wherein the neovascular disease is macular degeneration.

12. A method of treating neovascular disease of the eye, comprising:
- administering a conjugate to target neovascular tissue of the eye comprising:
  - a photosensitizing compound selected from the group consisting of chlorines, bacteriochlorophylls, phthalocyanines, porphyrins, purpurins, merocyanines, psoralens, porfimer sodium, delta-aminolevulinic acid protoporphyrin, indocyanine green, benzoporphyrin, methylene blue, toluidine blue, texaphyrins, pyropheophorbide compounds, and verteporfin; and
  - a targeting moiety that selectively binds to abnormal endothelium, wherein the targeting moiety consists of an antibody or an antibody fragment thereof that binds to a VEGF receptor;
- allowing sufficient time for the conjugate to clear from non-targeted tissue of the eye; and
- illuminating the eye with a light having a wave length or waveband absorbed by the targeted photosensitizing compound to activate the photosensitizing compound, and
- wherein the light has a combination of an intensity of light of less than 500 mW/cm$^2$ and a duration of illumination of about 4 minutes to about 10 minutes to produce a total fluence of light irradiation from between about 30 J/cm$^2$ to about 10,000 J/cm$^2$ which destroys the targeted neovascular tissue while the non-targeted tissue remains undamaged.

13. The method of claim 12, wherein the total fluence of light irradiation from between about 30 J/cm$^2$ to about 900 J/cm$^2$.

14. The method of claim 12, wherein the eye is illuminated with a light having a wave length or waveband that matches the excitation wave length or waveband of the targeted photosensitizing compound to activate the photosensitizing compound.

15. The method of claim 12, wherein the targeted neovascular tissue is present in retina, choroid or both.

16. The method of claim 12, wherein the neovascular disease is diabetic retinopathy.

17. The method of claim 12, wherein the neovascular disease is macular degeneration.

* * * * *